United States Patent [19]

Adam et al.

[11] Patent Number: 5,409,918
[45] Date of Patent: Apr. 25, 1995

[54] CRYSTALLINE CEPHEM ACID ADDITION SALTS AND PROCESS FOR THEIR PREPARATION

[75] Inventors: Friedhelm Adam, Hofheim am Taunus; Walter Dürckheimer, Hattersheim am Main; Burkhard Mencke, Holzappel; Dieter Isert, Eschborn, all of Germany

[73] Assignee: Hoechst Aktiengesellschaft, Frankfurt am Main, Germany

[21] Appl. No.: 931,505

[22] Filed: Aug. 21, 1992

Related U.S. Application Data

[63] Continuation of Ser. No. 778,745, Oct. 18, 1991, abandoned, which is a continuation of Ser. No. 536,273, Jun. 11, 1990, abandoned.

[30] Foreign Application Priority Data

Jun. 13, 1989 [DE] Germany ............... 39 19 259.8

[51] Int. Cl.$^6$ ............... C07D 501/32; A61K 31/545
[52] U.S. Cl. ............... 514/202; 540/222
[58] Field of Search ............... 514/201, 202; 540/222, 540/221

[56] References Cited

U.S. PATENT DOCUMENTS

| | | | |
|---|---|---|---|
| 4,098,888 | 6/1978 | Ochiai et al. | 424/246 |
| 4,203,899 | 5/1980 | Ochiai et al. | 548/194 |
| 4,205,180 | 5/1980 | Ochiai et al. | 560/168 |
| 4,264,595 | 4/1981 | Numata et al. | 424/246 |
| 4,278,793 | 7/1981 | Dürckheimer et al. | 544/27 |
| 4,283,396 | 8/1981 | Heymes et al. | 424/296 |
| 4,298,606 | 11/1981 | Ochiai et al. | 424/246 |
| 4,355,160 | 10/1982 | Ochiai et al. | 544/27 |
| 4,409,215 | 10/1983 | Takaya et al. | 424/246 |
| 4,462,999 | 7/1984 | Takaya et al. | 424/246 |
| 4,483,855 | 11/1984 | Nakao et al. | 424/246 |
| 4,486,425 | 12/1984 | Nakao et al. | 424/246 |
| 4,514,565 | 4/1985 | Ochiai et al. | 544/25 |
| 4,668,783 | 5/1987 | Ochiai et al. | 540/222 |
| 4,716,158 | 12/1987 | Nakao et al. | 540/222 |
| 4,904,652 | 2/1990 | Takaya et al. | 514/206 |
| 4,910,301 | 3/1990 | Kaplan et al. | 540/222 |
| 4,912,212 | 3/1990 | Ochiai et al. | 540/227 |
| 4,973,684 | 11/1990 | Ochiai et al. | 540/222 |
| 4,992,431 | 3/1991 | Heymes et al. | 514/202 |
| 5,026,695 | 6/1991 | Takaya et al. | 514/202 |
| 5,063,224 | 11/1991 | Mosher et al. | 514/202 |
| 5,100,887 | 3/1992 | Adam et al. | 514/195 |

FOREIGN PATENT DOCUMENTS

0034536A2 2/1981 European Pat. Off. .
0034536B1 2/1981 European Pat. Off. .

(List continued on next page.)

OTHER PUBLICATIONS

Chemical Abstracts vol. 115(8):78903(j) (1991).
Chemical Abstracts vol. 105(19):164392(s) (1986).
In Vivo Evaluation of Tigemonam, a Novel Oral Monobactam, Junius M. Clark et al., Antimicrobial (List continued on next page.)

Primary Examiner—Nicholas Rizzo
Attorney, Agent, or Firm—Finnegan, Henderson, Farabow, Garrett & Dunner

[57] ABSTRACT

Crystalline cephem acid addition salts of the general formula II

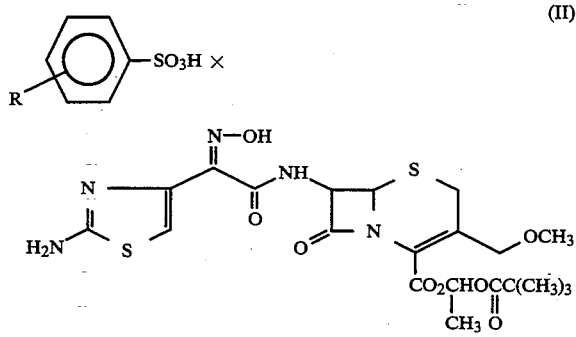

pharmaceutical preparations effective against bacterial infections which contain such cephem derivatives, processes for the preparation of the cephem derivatives and the pharmaceutical preparations, and the use of the cephem derivatives for combating bacterial infections.

9 Claims, No Drawings

FOREIGN PATENT DOCUMENTS

| | | |
|---|---|---|
| 0029557A2 | 3/1981 | European Pat. Off. |
| 0049119A2 | 4/1982 | European Pat. Off. |
| 0134420A1 | 3/1985 | European Pat. Off. |
| 2556736A1 | 6/1976 | Germany. |
| 2560398C2 | 9/1983 | Germany. |
| 3804841 | 8/1989 | Germany. |
| 3809561 | 10/1989 | Germany. |
| 3809561 | 10/1989 | Germany. |

OTHER PUBLICATIONS

Agents and Chemotherapy, vol. 31, No. 2, Feb. 1987, pp. 226–229.

Pharmacokinetic and In Vivo Studies with Azithromycin (CP-62,993), a New Macrolide with an Extended Half–Life and Excellent Tissue Distribution, Girard et al., Antimicrobial Agents and Chemotherapy, vol. 31, No. 12, Dec. 1987, pp. 1948–1954.

The Relationship of Absorption Characteristics and Gastrointestinal Side Effects of Oral Antimicrobial Agents, Grossman, Clinical Therapeutics, vol. 13, No. 1, pp. 189–193 (1991).

Uptake of the cephalosporin, cephalexin, by a dipeptide transport carrier in the human intestinal cell line, Caco-2, Dantzig et al., Biochimica et Biophysica Acta, 1027, pp. 211–217 (1990).

Stereochemical Considerations in Drug Absorption, Disposition and Pharmacokinetics, Hutt, Drug Chirality, 24th and 25th Oct. 1990.

Studies on Orally Active Cephalosporin Esters. IV.[1]), Miyauchi et al., Chem. Pharm. Bull. 32(12), pp. 3272–3276 (1989).

Studies on Orally Active Cephalosporin Esters. II.[1]), Miyauchi et al., Chem. Pharm. Bull. 37(9), pp. 2369–2374 (1989).

Synthesis and Mechanisms of Decomposition of Some Cephalosporin Prodrugs, Saab et al., Journal of Pharmaceutical Sciences, vol. 79, No. 9, (1990).

Orally Active 1-(Cyclohexyloxycarbonyloxy)Alkyl Ester Prodrugs of Cefotiam Nishimura et al., The Journal of Antibiotics, vol. XL, No. 1, pp. 81–90 (1986).

Angewandte Chemie, vol. 24, No. 3, Mar. 1985, pp. 180–202.

Pharmacokinetics of FK482, A New Orally Active Cephalosporin, in Animals, Sakamoto et al., The Journal of Antibiotics, vol. XLI, No. 12, pp. 1896–1905 (1988).

CRYSTALLINE CEPHEM ACID ADDITION SALTS AND PROCESS FOR THEIR PREPARATION

This application is a continuation of application Ser. No. 07/778,745, filed Oct. 18, 1990 now abandoned, which is itself a continuation of application Ser. No. 07/536,273, filed Jun. 11, 1990, now abandoned.

The invention relates to crystalline, enterally absorbable salts of α-(2,2-dimethylpropanoyloxy)ethyl 7-[2-(2-aminothiazol-4-yl)-2-(Z)-hydroxyimino-acetamido]-3-methoxymethyl-3-cephem-4-carboxylate of the formula I

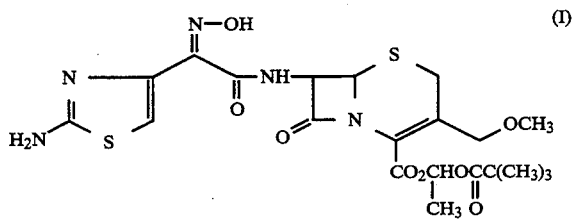

and a process for their preparation.

Many clinically relevant cephalosporins having a broad antimycrobial spectrum have already been developed. However, most are only suitable for parenteral administration, as they are only absorbed very inadequately, if at all after oral administration. In many cases it is desirable, however, to give highly active antibiotics to the patient in oral form. This form of therapy is simpler and considerably lowers the costs of the treatment.

In some cases it is possible to increase the absorption of a cephalosporin in the gastrointestinal tract by esterification of the 4-carboxyl group. Since the cephalosporin esters as a rule have no antibiotic activity per se, the ester components must be chosen so that, after absorption, the ester is split back again rapidly and completely to the cephalosporin having a free carboxyl group by enzymes specific to the body, such as esterases.

In German Patent Applications P 3,804,841 and P 3,809,561, a number of esters of 7-[2-(2-aminothiazol-4-yl)-2-(Z)-hydroxyimino-acetamido]-3-methoxymethyl-3-cephem-4-carboxylic acid are described which are readily absorbed enterally in different animal species. Of the esters described in German Patent Application P 3,804,841, it has been found that the ester of the formula I is of particular interest.

This ester has an asymmetric carbon atom in the 1-position of the 1-pivaloyl group and can therefore exist in the form of R- and S-isomers or mixtures thereof. The processes for the preparation of the ester of the formula I which are described in the German Patent Application P 3,804,841 produce the material in amorphous form. The two diastereomers have the same absorption.

Attempts to crystallize I from the customary organic solvents led to losses. In addition, the ratio of the two diastereomers, which have different solubilities, is shifted in the crystallization step.

In the light of the weak basicity of the amino group, the preparation of a salt of I is only successful if the ester of the formula I is reacted with strong acids. The processes for the preparation, of crystalline salts of all types of cephalosporin esters described in the patent literature and other literature did not lead to the desired result when used on the above compound. Thus, for example, the preparation of a hydrochloride, sulfate or phosphate led only to an amorphous product.

It was therefore surprising that, according to the invention, crystalline products were obtained.

The preparation of a crystalline ester or a crystalline salt which contains both isomers in an approximately ratio is, however, very worthy of effort. An operation of this type leads to an improvement in the purity, and to improved stability of the labile β-lactam esters. The purity can be determined from physicochemical parameters, such as, for example, high melting point, solubility, stability, and Δ3/Δ2 isomerization of the double bond. It is also possible in this way to obtain products of defined or reproducible composition in the cases in which solvents or other substances used in the salt preparation are incorporated or absorbed in the crystal lattice.

The invention relates to crystalline, stoichiometric and enterally absorbable salts of the general formula II

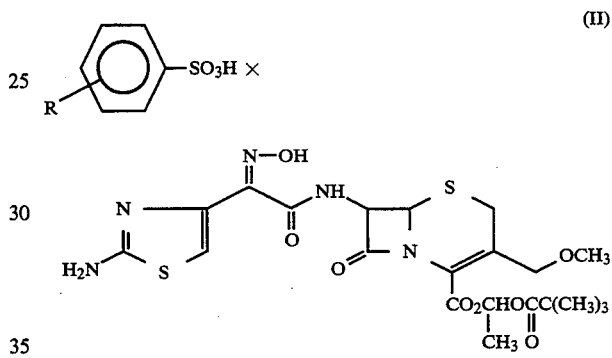

in which R stands for hydrogen or $C_1$–$C_4$-alkyl and the group =N— OH is in the syn-position.

If R has the meaning of $C_1$–$C_4$-alkyl, it can stand, for example, for methyl, ethyl, propyl, isopropyl, butyl, isobutyl or tert.-butyl. The meanings of hydrogen, methyl or ethyl are preferred for R, in particular of methyl or ethyl. R can be in the ortho, meta or para position, but preferably in the para position. Preferred acid addition salts are the benzenesulfonate, toluenesulfonate or p-ethylbenzenesulfonate.

The invention furthermore relates to a process for the preparation of compounds of the general formula II, which comprises reacting amorphous material of the formula I with acids of the general formula III

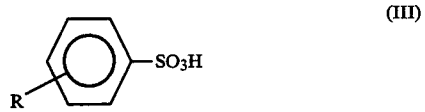

in which R has the above meaning, in an organic solvent and, if necessary, adding another organic solvent or water to this solution in order to initiate and/or complete the crystallization.

The acid component can be used in a small excess, preferably 1–1.5 equivalents relative to the ester of the formula I.

The choice of the solvent proves to be significant. In order to obtain an approximately 1:1 ratio of the two diastereomers, a solvent system must be chosen which ensures a virtually quantitative recovery of the salts.

Suitable solvents for the reaction are organic solvents immiscible with water such as, for example, ethyl acetate, n-butyl acetate or tert.-butyl acetate, but preferably those which, with respect to a later possibly necessary addition of water—are miscible with water.

Suitable organic, water-miscible solvents are, for example, $C_1$–$C_4$-alcohols, such as, for example, methanol, ethanol, isopropanol, propanol, butanol, 2-butanol, isobutanol, tert.-butanol, acetone, tetrahydrofuran or mixtures of these. Ethanol, propanol and acetone are particularly preferred. In order to complete the crystallization, a water-immiscible solvent such as, for example, n-hexane, toluene, diethyl ether or diisopropyl ether can be added to the suspension of the crystals in a mixture of water and the water-miscible solvent. An addition of solvent of this type is naturally also possible if the reaction has been carried out in a water-immiscible organic solvent.

In the water addition preferred according to the invention, the total amount of the added water is, for example, up to about 20-fold of the volume of the organic solution, but it can also be substantially higher.

The combination of the organic solution with the water or with another organic solvent is carried out slowly, for example dropwise, at such a rate that a good crystallinity of the product is achieved.

The crystallization is preferably carried out at room temperature. However, good results are also obtained at temperatures of, for example, 0° to 40° C. A subsequent stirring time of up to about 3 hours or more completes the crystallization.

The crystalline salts of the formula II thus obtained are separated off by customary laboratory methods, such as, for example, filtration, and freed from adhering solvent under a low vacuum.

If the crystals obtained by filtration are subjected to a high vacuum ($<1$ mm Hg), both organic solvent and water are removed, particularly in the presence of a drying agent such as, for example, concentrated sulfuric acid, phosphoric anhydride, and also caustic alkali or caustic soda, as well as silica gel.

Stability investigations carried out with the crystalline salts of the formula II show a substantial improvement stability compared to the base I.

Tests on various animal species have shown that the salts are also excellently enterally absorbed.

The compounds of the general formula II according to the invention are administered orally in the form of customary pharmaceutical preparations, such as, for example, capsules, tablets, powders, syrups or suspensions. The dose depends on the age, the symptoms and the body weight of the patient and on the duration of the treatment. However, as a rule it is between about 0.2 g and about 5 g daily, preferably between about 0.5 g and about 3 g daily. The compounds are preferably administered in divided doses, for example 2 to 4 times daily, where the individual dose may contain, for example between 50 and 500 mg of active compound.

The oral preparations may contain the customary excipients and/or diluents. Thus, for example, binders, such as, for example, gelatin, sorbitol, polyvinylpyrrolidone or carboxymethylcellulose, diluents, such as, for example, lactose, sugar, starch, calcium phosphate or polyethylene glycol and lubricants, such as, for example, talc or magnesium stearate are suitable for capsules or tablets, and, for example, aqueous or oily suspensions, syrups or similar known preparation forms are suitable for liquid preparations.

The following working examples for salts of the compound of the formula I, α-(2,2-dimethylpropanoyloxy)ethyl 7-[2-(2-aminothiazol 4-yl )-2-(Z)-hydroxyimino-acetamido]-3-methoxymethyl-3-cephem-4-carboxylate, which can be prepared according to the invention, serve to illustrate the invention further, without limiting it thereto.

WORKING EXAMPLES

Working Example 1

α-(2,2-Dimethylpropanoyloxy)ethyl 7-[2-(2-aminothiazol-4-yl)-2-(Z)-hydroxyimino-acetamido]-3-methoxymethyl-3-cephem-4-carboxylate benzenesulfonate A solution of 0.44 g (1 eq.) of benzenesulfonic acid in 9 ml of ethyl acetate was added dropwise to a solution of 1.5 g (2.77 mmol) of α-(2,2-dimethylpropanoyloxy)ethyl 7-[2-(2-aminothiazol-4-yl)-2-(Z)-hydroxyimino-acetamido]-3-methoxymethyl-3-cephem-4-carboxylate in 21 ml of ethyl acetate. After crystallization began, the mixture was stirred for a further 30 minutes, and the crystals were filtered off with suction and washed with a little diethyl ether. After drying over $CaCl_2$/paraffin in vacuo, 1.4 g of the desired title compound were obtained, which was identified as crystalline material under the polarization microscope and consisted of an approximately 1:1 mixture of the two diastereomers according to HPLC.

M.p.: from 198° C. (with decomposition). $^1$H NMR (270 MHz, DMSO-$d_6$): δ(ppm)=1.15 (9H, 2 x s, tert.butyl), 1.48 (1H, dd, CH($CH_3$)), 3.2 (3H, 2 x s, $OCH_3$), 3.47–3.7 (2H, 2 x dd, S-$CH_2$), 4.13 (2H, bs, 3'—$CH_2$), 5.21 (1H, 2 x d, J=6 Hz, 6-H ), 5.83 (1H, 2 x dd, J=6 HZ, 7-H), 6.8 (1H, 2 x s, thiazole-H), 6.9 (1H, dq, CH—$CH_3$), 7.3 (3H, m, arom. H ), 7.6 (2H, m, arom. H ), 9.65 (1H, d, NH), 12.05 (1H, bs, oxime-H). Elemental analysis $C_{27}H_{32}N_5O_{11}S_3$ calc. C 46.3 H 4.8 N 10.0 O 25.1 S 13.8 (699.78) found C 46.3 H 4.8 N 10.1 O 25.3 S 13.5

Working Example 2

α-(2,2-Dimethylpropanoyloxy)ethyl 7-[2-(2-aminothiazol-4-yl)-2-(Z)-hydroxyimino-acetamido]-3-methoxymethyl-3-cephem-4-carboxylate toluenesulfonate A solution of 570 mg (3 mmol) of p-toluenesulfonic acid in 1 ml of acetone was added to a solution of 1.08 g (2 mmol) of α-(2,2-dimethylpropanoyloxy)ethyl 7-[2-(2-aminothiazol-4-yl)-2-(Z)-hydroxyimino-acetamido]-3-methoxymethyl-3-cephem-4-carboxylate in 3 ml of acetone. 28 ml of water was then slowly added dropwise with stirring to the rapidly forming crystal suspension. The crystalline precipitate was then filtered off with suction, washed eight times with 3 ml of water and dried in vacuo over calcium chloride/paraffin. 1.08 g of the desired title compound were obtained, which consisted of an approximately 1:1 mixture of the two diastereomers according to HPLC and was characterized as crystalline under the polarization microscope. M.p.: from 190° C. (with decomposition).

$^1$H NMR (270 MHz, DMSO-$d_6$): δ(ppm)=1.15 (9H, 2 x s, tert.-butyl), 1.47 (1H, dd, CH—$CH_3$), 2.3 (3H, s, $CH_3$ on the aromatic ring), 3.2 (3H, 2 x s, $OCH_3$), 3.47–3.7 (2H, 2 x dd, S-$CH_2$), 4.13 (2H, bs, $CH_2$—$OCH_3$), 5.23 (1H, 2 x d, J=6 Hz, 6-H), 5.83 (1H, 2 x dd, J=6 HZ, 7-H), 6.83 (1H, 2 x s, thiazole-H), 6.9

(1H, dq, CH—CH₃), 7.1 and 7.5 (4H, d, arom. H), 9.68 (1H, d, NH), 12.08 (1H, bs, oxime-H). Elemental analysis $C_{28}H_{36}N_5O_{11}S_3$ calc. C 47.1 H 4.9 N 9.8 O 24.7 S 13.5 (713.80) found C 47.4 H 4.9 N 10.0 O 24.4 S 13.1

Working Example 3

α-(2,2-Dimethylpropanoyloxy)ethyl 7-[2-(2-aminothiazol-4-yl)-2-(Z)-hydroxyimino-acetamido]-3-methoxymethyl-3-cephem-4-carboxylate p-ethylbenzenesulfonate A solution of 664 mg of p-ethylbenzenesulfonic acid (3 mmol) in 1 ml of acetone was added to a solution of 1.08 g (2 mmol) of α-(2,2-dimethylpropanoyloxy)ethyl 7-[2-(2-aminothiazol-4-yl)-2-(Z)-hydroxyimino-acetamido]-3-methoxymethyl-3-cephem-4-carboxylate in 3 ml of acetone and 28 ml of water was then added slowly with stirring. After addition was complete, the mixture was seeded and stirred for 15 minutes. The crystalline precipitate was filtered off with suction, washed eight times with 3 ml of water each time and dried in vacuo over calcium chloride/paraffin. 1.28 g of the desired title compound was obtained, which consisted of an approximately 1:1 mixture of the two isomers according to HPLC and was characterized as crystalline under the polarization microscope.

M.p.: from 170° C. (with decomposition). ¹H NMR (270 MHz, DMSO-d₆): δ(ppm)=1.15 (9H, 2 x s, tert.-butyl), 1.17 (3H, t, CH₃CH₂—), 1.5 (3H, dd, CH—CH₃), 2.6 (2H, q, CH₃—CH₂—), 3.2 (3H, 2 x s, OCH₃), 3.47–3.7 (2H, 2 x dd, S-CH₂), 4.13 (2H, d, CH₂OCH₃), 5.23 (1H, 2 x d, J=6 Hz, 6-H), 5.83 (1H, 2 x dd, J=6 Hz, 6-H), 5.83 (1H, 2 x dd, J=6 HZ, 7-H), 6.83 (1H, 2 x s, thiazole-H), 6.9 (1H, dq, CH—CH₃), 7.15 and 7.51 (4H, d, arom. H), 9.67 (1H, d, NH), 12.05 (1H, bs, oxime-H). Elemental analysis $C_{29}H_{37}N_5O_{11}S_3$ calc. C 47.9 H 5.1 N 9.6 O 24.2 S 13.2 (727.86) found C 47.6 H 5.2 N 9.8 O 24.0 S 13.3

Working example 4

α-(2,2-dimethylpropanoyloxy)ethyl 7-[2-(2-aminothiazol-4-yl)-2-(Z)-hydroxyimino-acetamido]-3-methoxymethyl-3-cephem-4-carboxylate toluenesulfonate.

A solution of 2.1 g (11 mmol ) of p-toluenesulfonic acid in 5 ml of ethanol was added dropwise to a solution of 5 g (9.3 mmol) of α-(2,2-dimethylpropanoyloxy)ethyl 7-[2-(2-aminothiazol-4-yl)-2-(Z)-hydroxyimino-acetamido]-3-methoxymethyl-3-cephem-4-carboxylate in 32 ml of ethanol. After stirring at room temperature for 30 minutes, a total of 280 ml of diisopropyl ether were added to the crystal magma formed and the mixture was briefly stirred. The precipitate formed was then filtered off with suction and washed with a little diisopropyl ether, and the residue was dried in vacuo over calcium chloride/paraffin. 5.4 g of the desired crystalline title compound were obtained, which consisted of an approximately 1:1 mixture of the two diastereomers according to HPLC and was identical in its physical and chemical properties with the product from working example 2.

m.p.: from 190° C. (with decomposition).

Working example 5

α-(2,2-dimethylpropanoyloxy)ethyl 7-[2-(2-aminothiazol-4-yl)-2-(Z)-hydroxyimino-acetamido]-3-methoxymethyl-3-cephem-4-carboxylate toluenesulfonate A solution of 1.8 g (15 mmol) of p-toluenesulfonic acid in 5 ml of acetone was added dropwise to a solution of 5 g (9.3 mmol) of α-(2,2-dimethylpropanoyloxy)ethyl 7-[2-(2-aminothiazol-4-yl)-2-(Z)-hydroxyimino-acetamido]-3-methoxymethyl-3-cephem-4-carboxylate in 35 ml of acetone. After stirring briefly, a thick precipitate formed. After stirring for 15 minutes, a total of 185 ml of diisopropyl ether were slowly added dropwise to complete crystallization and the mixture was stirred for a short time. The precipitate was then filtered off with suction, washed with a little diisopropyl ether and dried in vacuo over calcium chloride/paraffin. 5.9 g of crystalline title compound were obtained, which consisted of an approximately 1:1 mixture of the two diastereomers according to HPLC and was identical in its physical and chemical properties with the product from working example 2.

m.p.: from 190° C. (with decomposition).

Working example 6

α-(2,2-Dimethylpropanoyloxy)ethyl 7-[2-(2-aminothiazol-4-yl)-2-(Z)-hydroxyimino-acetamido]-3-methoxymethyl-3-cephem-4-carboxylate toluenesulfonate A solution of 2.1 g (11 mmol) of p-toluenesulfonic acid in 5 ml of acetone was added dropwise to a solution of 5 g (9.3mmol) of α-(2,2-dimethylpropanoyloxy)ethyl 7-[2-(2-aminothiazol-4-yl)-2-(Z)-hydroxyimino-acetamido]-3-methoxymethyl-3-cephem-4-carboxylate in 35 ml of acetone. After stirring briefly, a precipitate formed, which process was completed by slowly adding 250 ml of t-butyl methyl ether. After stirring for 15 minutes, the crystalline product was filtered off with suction, washed with a little t-butyl methyl ether and dried in vacuo over calcium chloride/paraffin. 4.6 g of the desired crystalline title compound were obtained, which consisted of an approximately 1:1 ratio of the two diastereomers and was identical in its physical and chemical properties with the product from working example 2.

m.p.: from 190° C. (with decomposition).

We claim:

1. A crystalline cephem acid addition salt of the formula Ii

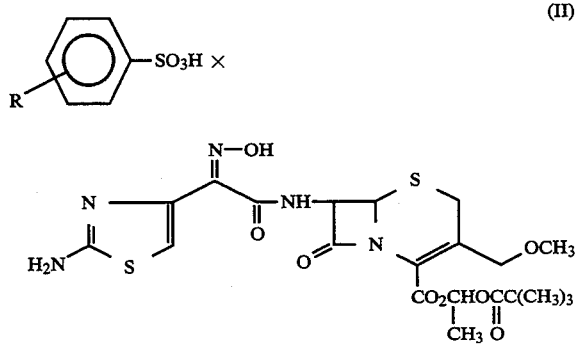

(II)

in which R stands for hydrogen or $C_1$–$C_4$-alkyl and the group =N—OH is in the syn position, wherein said crystalline salt exists in the form of a mixture of the 1S and 1R diastereomers resulting from the asymmetric carbon atom in the 1-position of the (2,2-dimethylpropanoyloxy)-ethyl group.

2. Crystalline α-(2,2-dimethylpropanoyloxy)-ethyl 7-[2-(2-aminothiazol-4-yl)-2-(Z)-hydroxyimino-acetamido)-3-methoxymethyl-3-cephem-4-carboxylate benzenesulfonate, wherein said crystalline salt exists in the form of a mixture of the 1S and 1R diastereomers resulting from the asymmetric carbon atom in the 1-position of the (2,2-dimethylpropanoyloxy)-ethyl group.

3. Crystalline α-(2,2-dimethylpropanoyloxy)-ethyl 7-[2-(2-aminothiazol-4-yl)-2-(Z)-hydroxyimino-acetamido)-3-methoxymethyl-3-cephem-4-carboxylate toluenesulfonate, wherein said crystalline salt exists in the form of a mixture of the 1S and 1R diastereomers resulting from the asymmetric carbon atom in the 1-position of the (2,2-dimethylpropanoyloxy)-ethyl group.

4. Crystalline α-(2,2-dimethylpropanoyloxy)-ethyl 7-[2-(2-aminothiazol-4-yl)-2-(Z)-hydroxyimino-acetamido)-3-methoxymethyl-3-cephem-4-carboxylate p-ethylbenzenesulfonate, wherein said crystalline salt exists in the form of a mixture of the 1S and 1R diastereomers resulting from the asymmetric carbon atom in the 1-position of the (2,2-dimethylpropanoyloxy)-ethyl group.

5. A pharmaceutical preparation effective against bacterial infections comprising an antibiotically effective amount of the crystalline cephem acid addition salt of the formula II

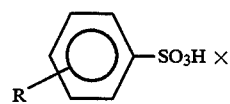

(II)

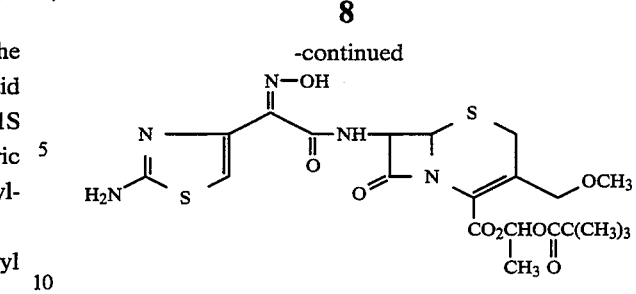

in which R stands for hydrogen or $C_1$–$C_4$-alkyl and the group =N—OH is in the syn position, wherein said crystalline salt exists in the form of a mixture of the 1S and 1R diastereomers resulting from the asymmetric carbon atom in the 1-position of the (2,2-dimethylpropanoyloxy)-ethyl group.

6. A method for combating bacterial infections comprising administering to an animal host in an antibiotically effective amount the crystalline cephem acid addition salts of the formula II (II)

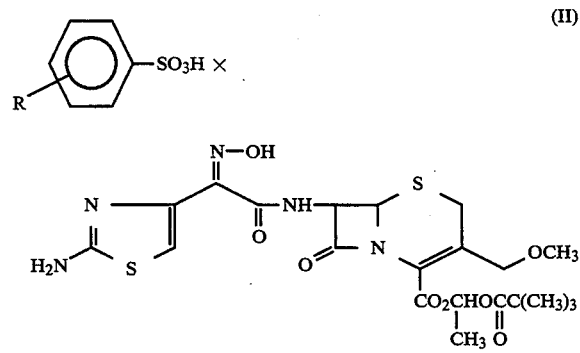

in which R stands for hydrogen or $C_1$–$C_4$-alkyl and the group =N—OH is in the syn position, wherein said crystalline salt exists in the form of a mixture of the 1S and 1R diastereomers resulting from the asymmetric carbon atom in the 1-position of the (2,2-dimethylpropanoyloxy)-ethyl group, said animal host being in recognized need of treatment for a bacterial infection.

7. The crystalline acid addition salt of claim 1, wherein said two diastereomers exist in an approximately 1:1 ratio.

8. The pharmaceutical preparation of claim 5, wherein said two diastereomers exist in an approximately 1:1 ratio.

9. The method of claim 6, wherein said two diastereomers exist in an approximately 1:1 ratio.

* * * * *

UNITED STATES PATENT AND TRADEMARK OFFICE
CERTIFICATE OF CORRECTION

PATENT NO. : 5,409,918
DATED : April 25, 1995
INVENTOR(S) : Friedhelm ADAM et al It is certified that error appears in the above-indentified patent and that said Letters Patent is hereby corrected as shown below:

Claim 1, Column 6, Line 52, "Ii" should read --II--.

Signed and Sealed this

First Day of August, 1995

Attest:

BRUCE LEHMAN

*Attesting Officer*     *Commissioner of Patents and Trademarks*